US010315054B2

(12) United States Patent
Mead et al.

(10) Patent No.: US 10,315,054 B2
(45) Date of Patent: Jun. 11, 2019

(54) METHOD OF CALIBRATING A PATIENT MONITORING SYSTEM FOR USE WITH A RADIOTHERAPY TREATMENT APPARATUS

(71) Applicant: VISION RT LIMITED, London (GB)

(72) Inventors: Edward William Mead, London (GB); Ivan Daniel Meir, London (GB)

(73) Assignee: VISION RT LIMITED, London (GB)

( * ) Notice: Subject to any disclaimer, the term of this patent is extended or adjusted under 35 U.S.C. 154(b) by 0 days.

(21) Appl. No.: 15/525,847

(22) PCT Filed: Nov. 9, 2015

(86) PCT No.: PCT/GB2015/053382
§ 371 (c)(1),
(2) Date: May 10, 2017

(87) PCT Pub. No.: WO2016/075445
PCT Pub. Date: May 19, 2016

(65) Prior Publication Data
US 2017/0319874 A1 Nov. 9, 2017

(30) Foreign Application Priority Data
Nov. 10, 2014 (GB) .................................. 1419936.8

(51) Int. Cl.
*A61N 5/10* (2006.01)
*G06T 7/80* (2017.01)
*H04N 13/204* (2018.01)

(52) U.S. Cl.
CPC ......... *A61N 5/1075* (2013.01); *A61N 5/1049* (2013.01); *G06T 7/85* (2017.01);
(Continued)

(58) Field of Classification Search
CPC .......... A61N 2005/1059; A61N 5/1049; A61N 5/1048; A61N 5/1075; A61N 2205/1059;
(Continued)

(56) References Cited

U.S. PATENT DOCUMENTS 6,327,331 B1 * 12/2001 Toth .................. A61B 6/08
378/20
7,348,974 B2 3/2008 Smith et al.
(Continued)

FOREIGN PATENT DOCUMENTS

WO 2014057280 A1 4/2014
WO 2015008040 A2 1/2015

OTHER PUBLICATIONS

International Search Report and Written Opinion of the International Searching Authority dated Feb. 15, 2016 to International Application No. PCT/GB2015/053382.
(Continued)

*Primary Examiner* — Kenny A Cese
(74) *Attorney, Agent, or Firm* — Birch, Stewart, Kolasch & Birch, LLP

(57) ABSTRACT

Some embodiments are directed to an image director of a patient monitoring system to obtain calibration images of a calibration sheet or other calibration object at various orientations and locations. The images are then stored and processed to calculate camera parameters defining the location and orientation of the image detector and identifying internal characteristics of the image detector, and the information are stored. The patient monitoring system can be re-calibrated by using the image detector to obtain an additional image of a calibration sheet or calibration object. The additional image and the stored camera parameters are then used to detect any apparent change in the internal characteristics of the image detector (10) (S6-4).

14 Claims, 7 Drawing Sheets

(52) U.S. Cl.
CPC ... *H04N 13/204* (2018.05); *A61N 2005/1059* (2013.01); *G06T 7/80* (2017.01); *G06T 2207/30208* (2013.01); *G06T 2207/30244* (2013.01)

(58) Field of Classification Search
CPC ... G06T 2207/30244; G06T 7/30; G06T 7/85; G06T 2207/30208; G06T 7/80; G01T 1/29; H04N 13/246; H04N 13/204
See application file for complete search history.

(56) References Cited

U.S. PATENT DOCUMENTS

| | | | |
|---|---|---|---|
| 7,889,906 B2 | 2/2011 | Smith et al. | |
| 8,135,201 B2 | 3/2012 | Smith et al. | |
| 8,353,628 B1* | 1/2013 | Yun | H01J 37/244 378/207 |
| 9,734,419 B1* | 8/2017 | Ye | G06T 7/00 |
| 2009/0052760 A1* | 2/2009 | Smith | A61N 5/1049 382/132 |
| 2009/0187112 A1 | 7/2009 | Meir et al. | |
| 2010/0259624 A1 | 10/2010 | Li et al. | |
| 2014/0063252 A1* | 3/2014 | Zhao | H04N 17/002 348/148 |
| 2014/0313347 A1 | 10/2014 | Wu et al. | |

OTHER PUBLICATIONS

Combined Search and Examination Report under Sections 17 and 18(3) dated May 13, 2015 in GB Application No. GB1419936.8.
Wu, Ziyan, et al., "Keeping a Pan-Tilt-Zoom Camera Calibrated", IEEE Transactions on Pattern Analysis and Machine Intelligence, IEEE Computer Society, USA, vol. 35, No. 8, Aug. 2013, pp. 1994-2007.
Tsai, R., "A versatile camera calibration technique for high-accuracy 3D machine vision metrology using off-the-shelf TV cameras and lenses", IEEE Journal of Robotics and Automation, USA, vol. 3, No. 4, Aug. 1, 1987, pp. 323-344.
Halcon the Power of Machine Vision, Solution Guide III-C 3D Vision, MVTec Software GmbH, Germany, 2013, pp. 1-242.

* cited by examiner

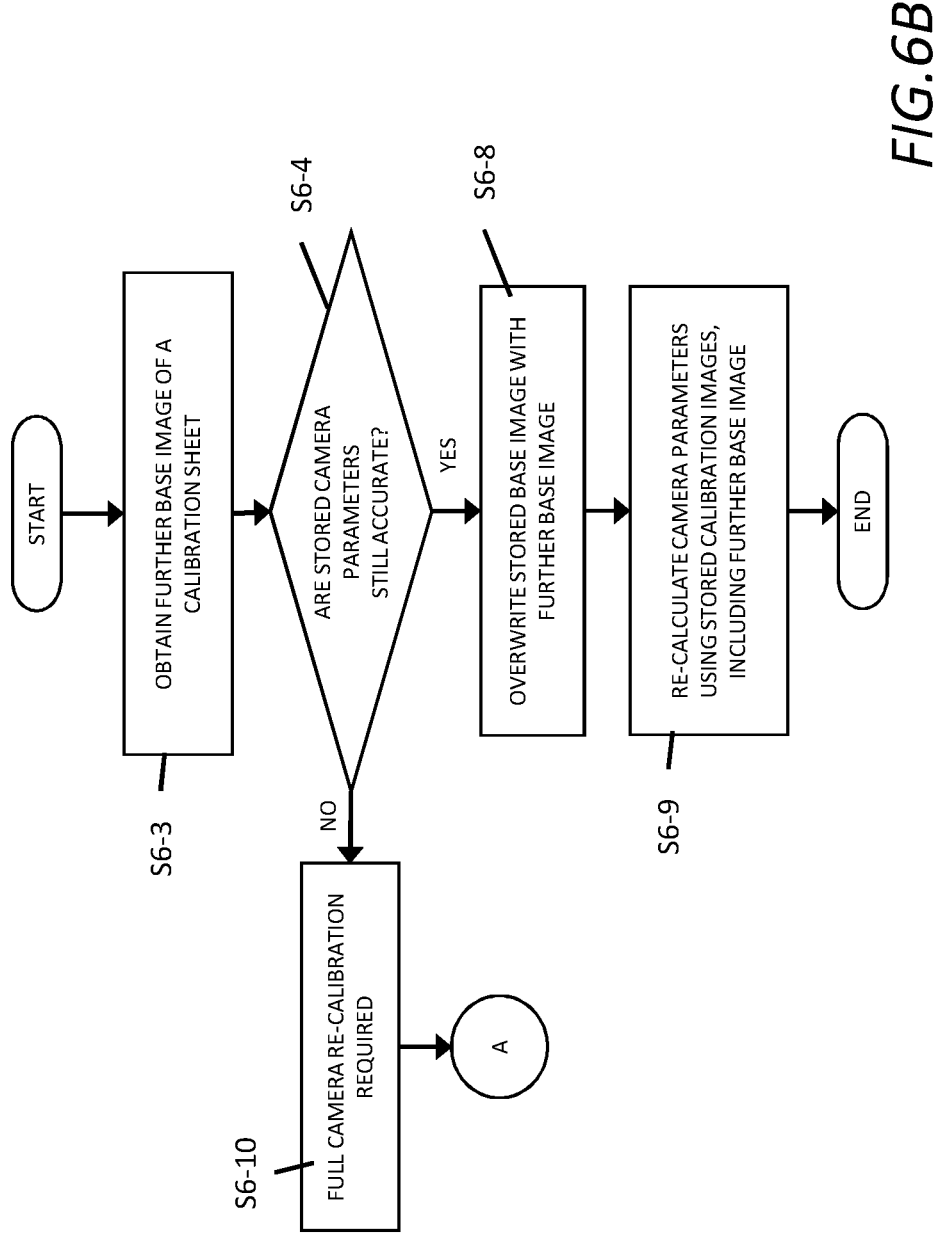

METHOD OF CALIBRATING A PATIENT MONITORING SYSTEM FOR USE WITH A RADIOTHERAPY TREATMENT APPARATUS

CROSS REFERENCE TO RELATED APPLICATION

This application is a National Phase filing under 35 C.F.R. § 371 of and claims priority to PCT Patent Application No.: PCT/GB2015/053382, filed on Nov. 9, 2015, which claims the priority benefit under 35 U.S.C. § 119 of British Application No.: 1419936.8, filed on Nov. 10, 2014, the contents of which are hereby incorporated in their entireties by reference.

BACKGROUND

Some embodiments relate to a method of calibrating a patient monitoring system for monitoring the location of a patient during radio therapy. In particular, some embodiments of the present invention concern a method of calibrating a stereoscopic camera system for use with a radiotherapy treatment apparatus and the like where accurate positioning and the detection of patient movement is important for successful treatment.

Radiotherapy involves projecting onto a predetermined region of a patient's body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

When applying radiation to a patient, the gating of treatment apparatus should be matched with the breathing cycle so that radiation is focused on the location of a tumour and collateral damage to other tissues is minimised. If movement of a patient is detected the treatment should be halted to avoid irradiating areas of a patient other than a tumour location.

For this reason a number of monitoring systems for assisting the positioning of patients during radiotherapy have therefore been proposed such as those described in Vision RT's earlier patents and patent applications U.S. Pat. Nos. 7,889,906, 7,348,974, 8,135,201, US2009/187112, WO2014/057280, and WO2015/008040 all of which are hereby incorporated by reference.

In the systems described in Vision RT's patent applications, stereoscopic images of a patient are obtained and processed to generate data identifying 3D positions of a large number of points corresponding to points on the surface of an imaged patient. Such data can be compared with data generated on a previous occasion and used to position a patient in a consistent manner or provide a warning when a patient moves out of position. Typically such a comparison involves undertaking Procrustes analysis to determine a transformation which minimises the differences in position between points on the surface of a patient identified by data generated based on live images and points on the surface of a patient identified by data generated on a previous occasion.

Treatment plans for the application of radiotherapy are becoming increasingly complex with treatment apparatus having multiple or floating iso-centres. Also, there is an increasing trend to make use of higher doses of radiation during treatment in order to reduce overall treatment time. Such increasing complexity and higher dosages bring with them the increasing possibility of mistreatment. There is therefore an ever increasing need for improvements in the accuracy of patient monitoring systems.

To obtain a reasonable field of view, in a patient monitoring system, cameras monitoring a patient typically view a patient from a distance (e.g. 1 to 2 meters from the patient being monitored). Vision RT's patient monitoring systems are able to generate highly accurate (e.g. sub millimeter) models of the surface of a patient. To do so, it is essential that the monitoring system is calibrated in order to establish camera parameters identifying the relative locations and orientations of the image capture devices/cameras, any optical distortion caused by the optical design of the lens of each image detector/camera e.g. barrel, pincushion, and moustache distortion and de-centring/tangential distortion, and other internal parameters of the cameras/image capture devices (e.g. focal length, image centre, aspect ratio skew, pixel spacing etc.). Once known, camera parameters can be utilised to manipulate obtained images to obtain images free of distortion. 3D position measurements can then be determined by matching corresponding portions in images obtained from different locations and deriving 3D positions from those matches and the relative locations and orientations of the image capture devices/cameras.

Typically, calibration of a patient monitoring system involves capturing multiple images of a calibration object of known size and with a known arrangement of calibration markings at various orientations and various locations within the field of view, and processing the images using information regarding the expected locations of the markings on the calibration object to determine the various parameters. The accuracy of the calibration then very much depends on the number of images used in the calibration process. The greater the number of images used, and the greater the variation in the orientation of the calibration plate between the various images, the more accurate the results. For example, the HALCON machine vision software package from MVTec Software GmbH requires at least 10 to 15 images of a calibration plate, and may require significantly more than this if the calibration object is small relative to the field of view of the image capture devices/cameras. As a consequence of the number of images that are required to be captured, it can be a time consuming to calibrate a computer vision system using such processes.

When a computer vision system is used for monitoring the positioning of patients during radiotherapy treatment, a system needs to be re-calibrated very frequently (ideally for each individual patient treatment session) to ensure that the parameters used to process captured images and generate computer models accurately reflect the current relative locations of the stereoscopic cameras. The need for high accuracy and regular re-calibration is exacerbated in the case of patient monitoring system where patients are viewed from a distance as very small changes in the orientations of the cameras can have a significant impact on the accuracy of models. Due to this sensitivity very regular calibration is particularly important for patient monitoring systems particularly where cameras may accidentally be knocked or change orientation, for example in areas that are prone to earthquakes such as California or Japan small earthquake tremors could cause movement of the image capture devices/cameras of the system leading to errors in patient positioning and treatment. However, where such calibration is undertaken at the desired frequency this has an adverse effect upon the throughput of patient treatment.

SUMMARY

It is therefore desirable to enhance the efficiency with which calibration procedures can be implemented for a patient monitoring system that is used with a radio therapy treatment apparatus.

In accordance with one aspect of the present invention there is provided a method of calibrating a patient monitoring system.

Initially, an image detector of the patient monitoring system is used to obtain a set of calibration images comprising images of a calibration object at various orientations and locations. These obtained calibration images are then stored and processed to calculate camera parameters defining the location and orientation of the image detector and parameters identifying internal characteristics of the image detector (e.g. lens distortion, focal length, aspect ratio etc.).

Subsequently the patient monitoring system is re-calibrated by using the image detector to obtain an additional image of the calibration object. This additional image and the stored camera parameters are then used to detect any apparent change in the internal characteristics of the image detector. If a change in the internal characteristics of an image detector is detected, a further set of calibration images using the image detector are obtained and the camera parameters for the image detector are recalculated using the further set of calibration images. If no apparent change in the parameters internal to an image detector is detected, the recalibration of the patient monitoring system is achieved by recalculating the camera parameters for the image detector using the stored set of calibration images and the additional image of the calibration object obtained by the image detector.

The process described above provides a means for quickly confirming the accuracy of a patient monitoring system that therefore facilitates improved efficiency of the calibration procedures. This is because rather than performing a complete recalibration of the system based on multiple images, only a single additional image is obtained and the camera correction parameters are recalculated using this single new image and the previously stored images from the original calibration. This reduces the amount of work necessary to perform the re-calibration process and thus assists with maintaining throughput using the treatment apparatus.

If internal characteristics of an image detector are adjusted then the system will no longer be accurate unless internal parameters are updated. If any change in internal characteristics of an image detector whether actual or apparent can be detected this will indicate that a full re-calibration needs to be undertaken. In contrast, if camera parameters relating to internal characteristics can be confirmed as accurate then accurate camera parameters for the relative locations and orientation of an image detector can be determined based on the appearance of a calibration object of known dimensions in an image taken with a camera and using the current internal parameters.

Detecting a change in the internal characteristics of an image detector can be achieved in a number of ways.

In some embodiments, detecting a change in internal characteristics of an image detector may comprise comparing stored camera parameters determined using the stored calibration images and camera parameters determined using the stored calibration images and an additional image, and determining whether any of the parameters identifying internal characteristics of the image detector differ by more than a threshold amount.

Alternatively in other embodiments, detecting an apparent change in internal characteristics of an image detector may comprise processing an additional image utilising the stored camera parameters to determine the location and orientation of the calibration object relative to the image detector, determining a back-projection of the expected appearance of the calibration object onto the image plane of the image detector utilising the stored camera parameters and the determined location and orientation of the calibration sheet; and comparing the appearance of the calibration object within the additional image captured by the image capture detector with the back-projection of the expected appearance of the calibration object.

Recalculating the camera parameters for an image detector using the stored set of calibration images and an additional image of the calibration object obtained by the image detector may comprise calculating the location and orientation of the image detector and internal characteristics of the image detector utilising the additional image as a base image relative to which the other images are compared.

In some embodiments, the calibration object may comprise a calibration sheet and the additional image may comprise an image of the calibration sheet located directly on a measurement plane of the patient monitoring system where the measurement plane of the patient monitoring system is defined as z=0 plane of a global co-ordinate system defined for the patient monitoring system. In such embodiments the global co-ordinate system defined for the patient monitoring system may be that used to generate 3D wire mesh models of the surface of a patient monitored by the system.

In some embodiments the set of calibration images used to calibrate the system may comprise at least 10 images of a calibration object at various orientations and various locations within a field of view of an image detector.

The method may be used to calibrate a patient monitoring system comprising a stereoscopic camera system having a plurality of image detectors, wherein each of the image detectors is calibrated in the manner described above.

The above described method of calibrating a patient monitoring system may be performed wherein the re-calibration is repeated periodically, with the monitoring system being used to monitor the position of a patient between obtaining images of the calibration object and the re-calibration of the patient monitoring system.

BRIEF DESCRIPTION OF THE DRAWINGS

An embodiment of the present invention will now be described in greater detail with reference to the accompanying drawings in which:

FIG. 6A-B is a flow diagram of a calibration method in accordance with the present invention.

DETAILED DESCRIPTION OF THE PREFERRED EMBODIMENTS

Prior to describing a method of operating a patient monitoring system for use with a radio therapy treatment apparatus, a patient monitoring system and radiotherapy treatment apparatus will be described.

Figure 1:
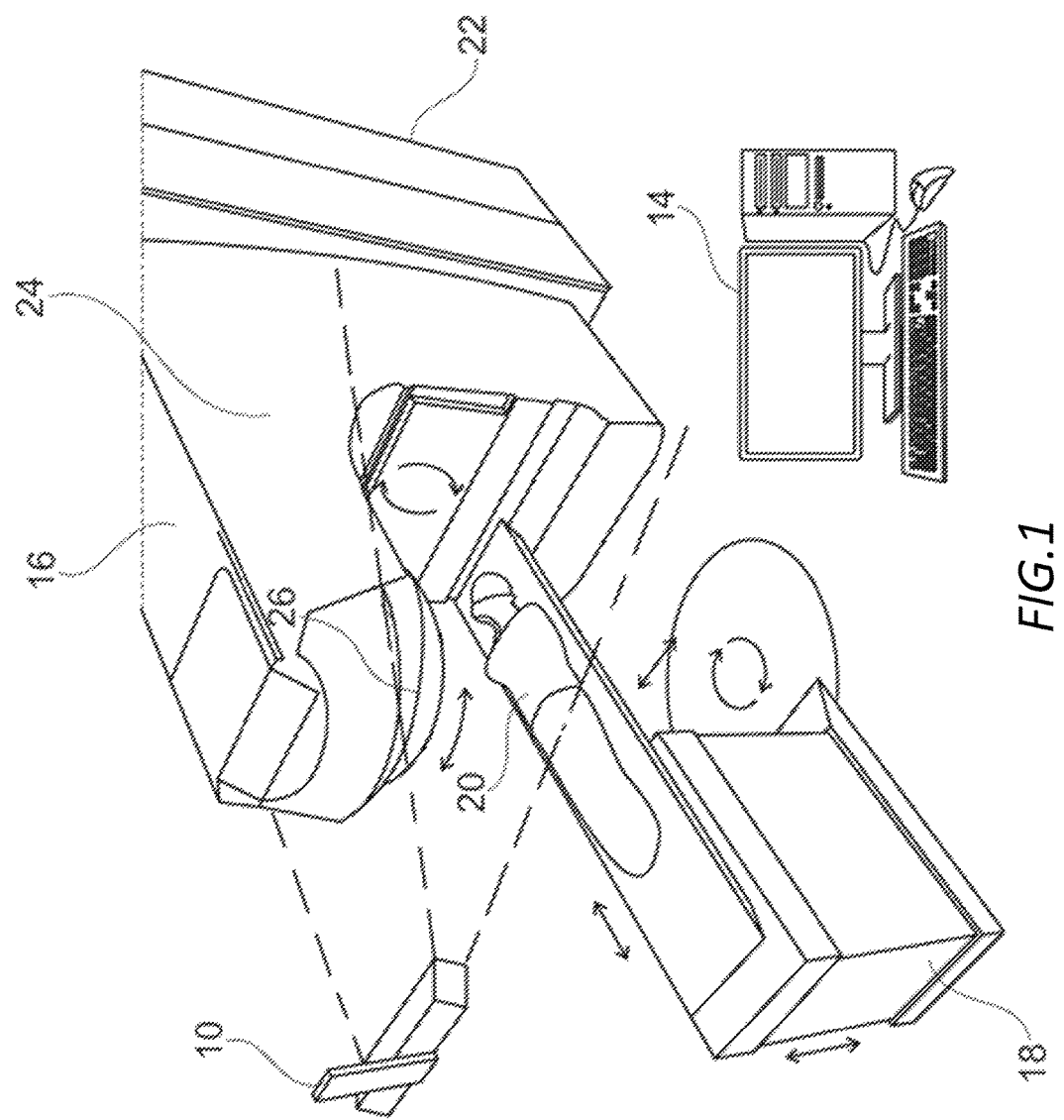
FIG. 1 is a schematic perspective view of a patient monitor.

FIG. 1 is a schematic perspective view of an exemplary patient monitoring system comprising a stereoscopic camera system 10 that is connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 comprises a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the centre of the main body 22 of the treatment apparatus 16. Additionally the location of irradiation by the treatment apparatus may also be varied by rotating the collimator 26 at the end of the gantry 24.

In use, the stereoscopic cameras 10 obtain video images of a patient 20 lying on the mechanical couch 18. These video images are passed via the wiring to the computer 14. The computer 14 then processes the images of the patient 20 to generate a model of the surface of the patient. This model is compared with a model of the patient generated during earlier treatment sessions. When positioning a patient the difference between a current model surface and a target model surface obtained from an earlier session is identified and the positioning instructions necessary to align the surfaces are determined and sent to the mechanical couch 18. Subsequently during treatment any deviation from an initial set up can be identified and if the deviation is greater than a threshold, the computer 14 sends instructions to the treatment apparatus 16 to cause treatment to be halted until a patient 20 can be repositioned.

Figure 2:
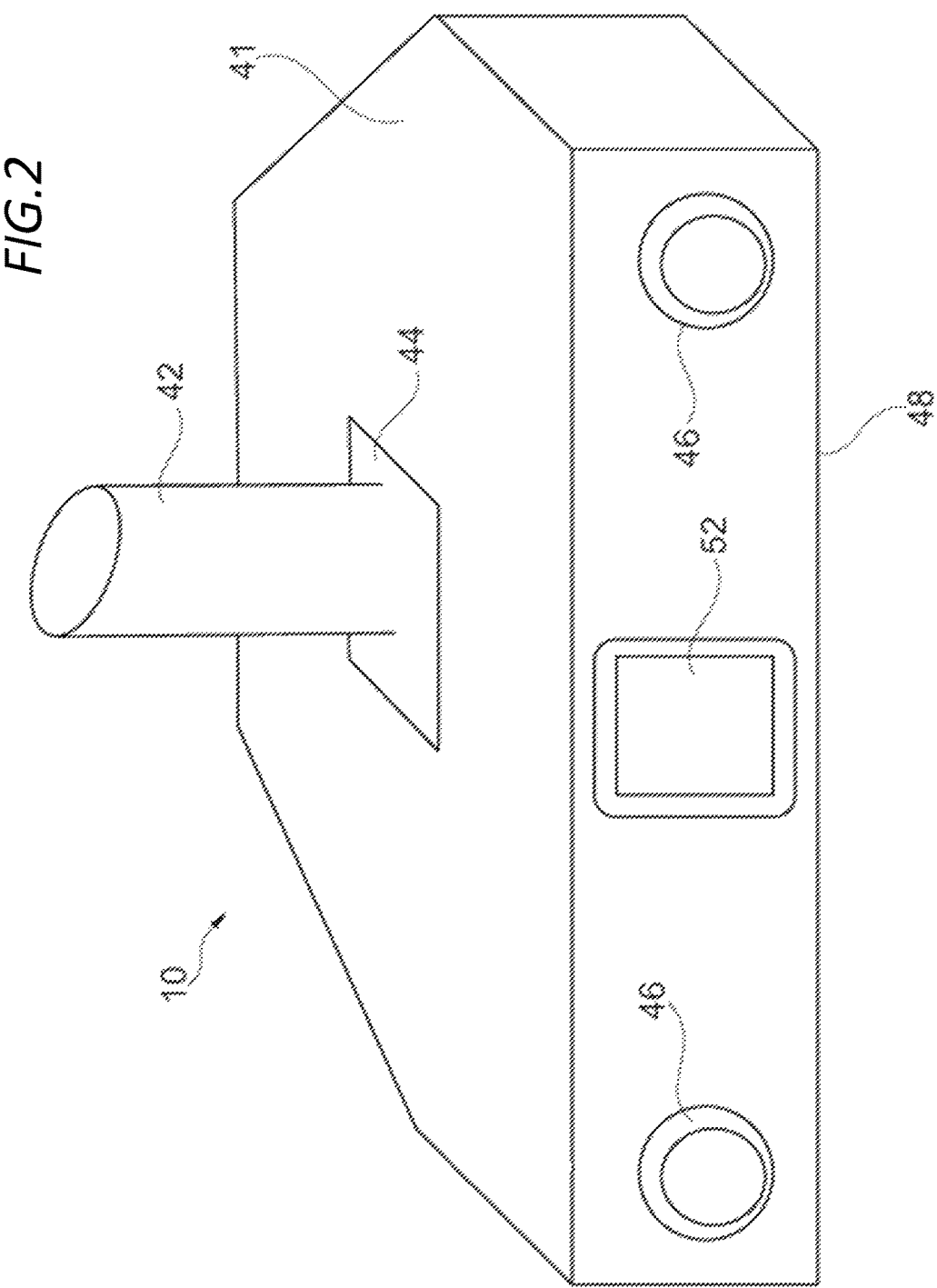
FIG. 2 is a front perspective view of the camera system of the patient monitor of FIG. 1.

FIG. 2 is a front perspective view of a stereoscopic camera system 10 of the patient monitoring system of FIG. 1.

In this embodiment the stereoscopic camera system 10 comprises a housing 41 which is connected to a bracket 42 via a hinge 44. The bracket 42 enables the stereoscopic camera system 10 to be attached in a fixed location to the ceiling of a treatment room whilst the hinge 44 permits the orientation of the stereoscopic camera system 10 to be orientated relative to the bracket 42 so that the stereoscopic camera system 10 is arranged to view a patient 20 on a mechanical couch 18.

A pair of lenses 46 are mounted at either end of the front surface 48 of the housing 41. These lenses 46 are positioned in front of image capture devices/cameras such as CMOS active pixel sensors or charge coupled devices (not shown) contained within the housing 41. The cameras/image detectors are arranged behind the lenses 46 so as to capture images of a patient 20 via the lenses 46.

A speckle projector 52 is provided in the middle of the front surface 48 of the housing 41 between the two lenses 46. The speckle projector 52 is arranged to illuminate a patient 20 with a non-repeating speckled pattern of red light so that when images of a patient 20 are captured by the two image detectors corresponding portions of captured images can be distinguished. To that end the speckle projector comprises a light source such as a LED and a film with a random speckle pattern printed on the film. In use light from the light source is projected via the film and as a result a pattern consisting of light and dark areas is projected onto the surface of a patient 20. When images of the projected speckle pattern are captured by the stereoscopic camera system 10 the images can then be processed to determine the positions of a set of points on the surface of the patient and hence the positioning of the patient can be monitored.

Figure 3:
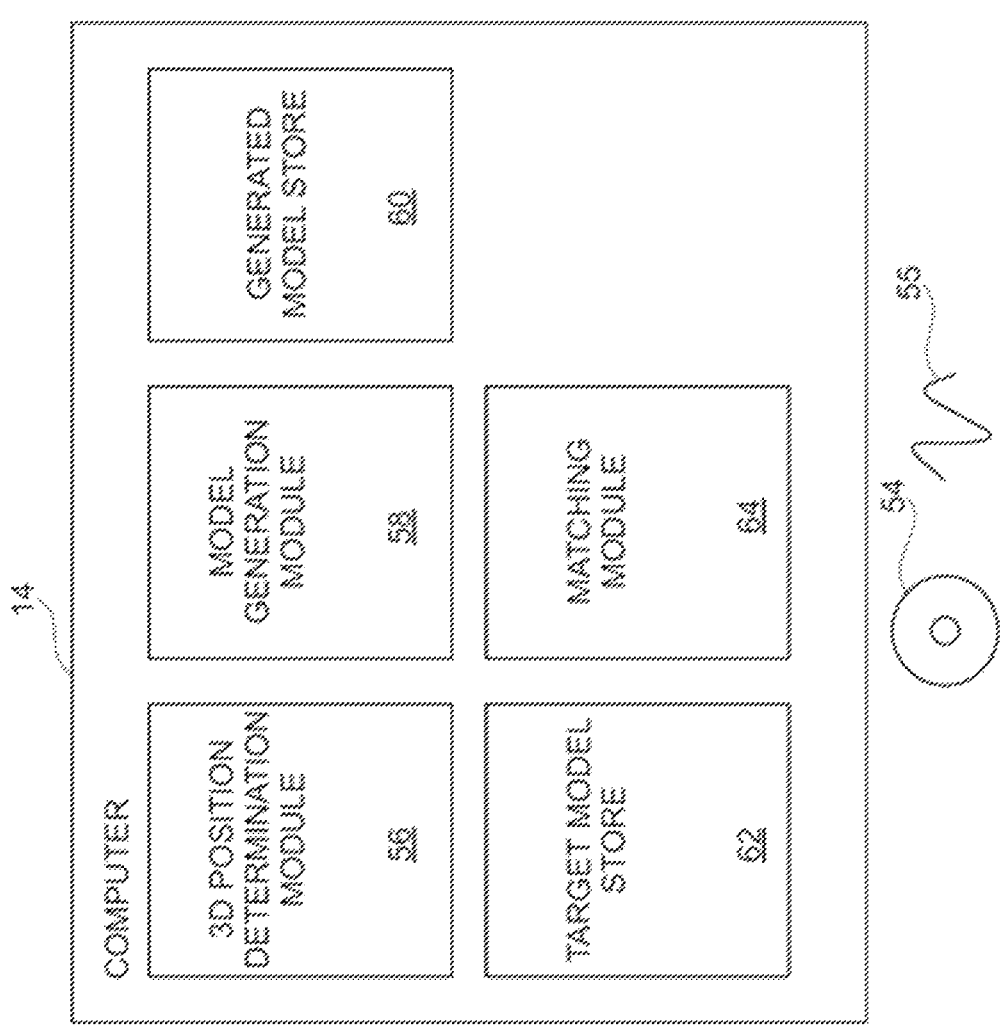
FIG. 3 is a schematic block diagram of the computer system of the patient monitor of FIG. 1.

FIG. 3 is a schematic block diagram of the computer 14 of the patient monitor of FIG. 1.

In order for the computer 14 to process images received from the stereoscopic camera system 10, the computer 14 is configured by software either provided on a disk 54 or by receiving an electrical signal 55 via a communications network into a number of functional modules 56-64. In this example, the functional modules 56-64 comprise: a 3D position determination module 56 for processing images received from the stereoscopic camera system 10, a model generation module 58 for processing data generated by the 3D position determination module 56 and converting the data into a 3D wire mesh model of an imaged computer surface; a generated model store 60 for storing a 3D wire mesh model of an imaged surface; a target model store 62 for storing a previously generated 3D wire mesh model; and a matching module 64 for determining rotations and translations required to match a generated model with a target model.

In use, as images are obtained by the stereoscopic camera system 10, these images are processed by the 3D position determination module 56. This processing enables the 3D position determination module to identify 3D positions of corresponding points in pairs of images on the surface of a patient 20. This is achieved by the 3D position determination module 56 identifying corresponding points in pairs of images obtained by the stereoscopic camera system 10 and then determining 3D positions for those points based on the relative positions of corresponding points in obtained pairs of images and stored camera parameters for each of the image capture devices/cameras of the stereoscopic camera system 10.

Typically the identification of corresponding points is based on analysis of image patches of around 16×16 pixels. In order to assist with identifying and matching corresponding patches as has been described the stereoscopic camera system 10 includes a speckle projector 52 arranged to project a random or quasi random speckle pattern onto the patient 20 being imaged so that different portions of the surface of the patient 20 can be more easily distinguished. The size of the speckle pattern is selected so that different patterns will be apparent in different image patches.

The position data generated by the 3D position determination module 56 is then passed to the model generation module 58 which processes the position data to generate a 3D wire mesh model of the surface of a patient 20 imaged by the stereoscopic cameras 10. In this embodiment the 3D model comprises a triangulated wire mesh model where the vertices of the model correspond to the 3D positions determined by the 3D position determination module 56. When such a model has been determined it is stored in the generated model store 60.

When a wire mesh model of the surface of a patient 20 has been stored, the matching module 64 is then invoked to determine a matching translation and rotation between the generated model based on the current images being obtained by the stereoscopic cameras 10 and a previously generated model surface of the patient stored in the target model store 62. The determined translation and rotation can then be sent as instructions to the mechanical couch 18 to cause the couch to position the patient 20 in the same position relative to the treatment apparatus 16 as they were when they were previously treated.

Subsequently, the stereoscopic cameras 10 can continue to monitor the patient 20 and any variation in position can be identified by generating further model surfaces and comparing those generated surfaces with the target model stored in the target model store 62. If it is determined that a patient has moved out of position, the treatment apparatus 16 can be halted and the patient 20 repositioned, thereby avoiding irradiating the wrong parts of the patient 20.

In order to construct models of the surface of a patient with as great an accuracy as possible, the patient monitoring system/stereoscopic camera system needs to be calibrated so that matching portions of images can be converted into a determination of 3D positions. This involves determining the relative positioning of the image capture devices. Additionally the calibration of the system must correct for any image distortion introduced by the lenses 46 or otherwise by the image capture devices.

Figure 4:
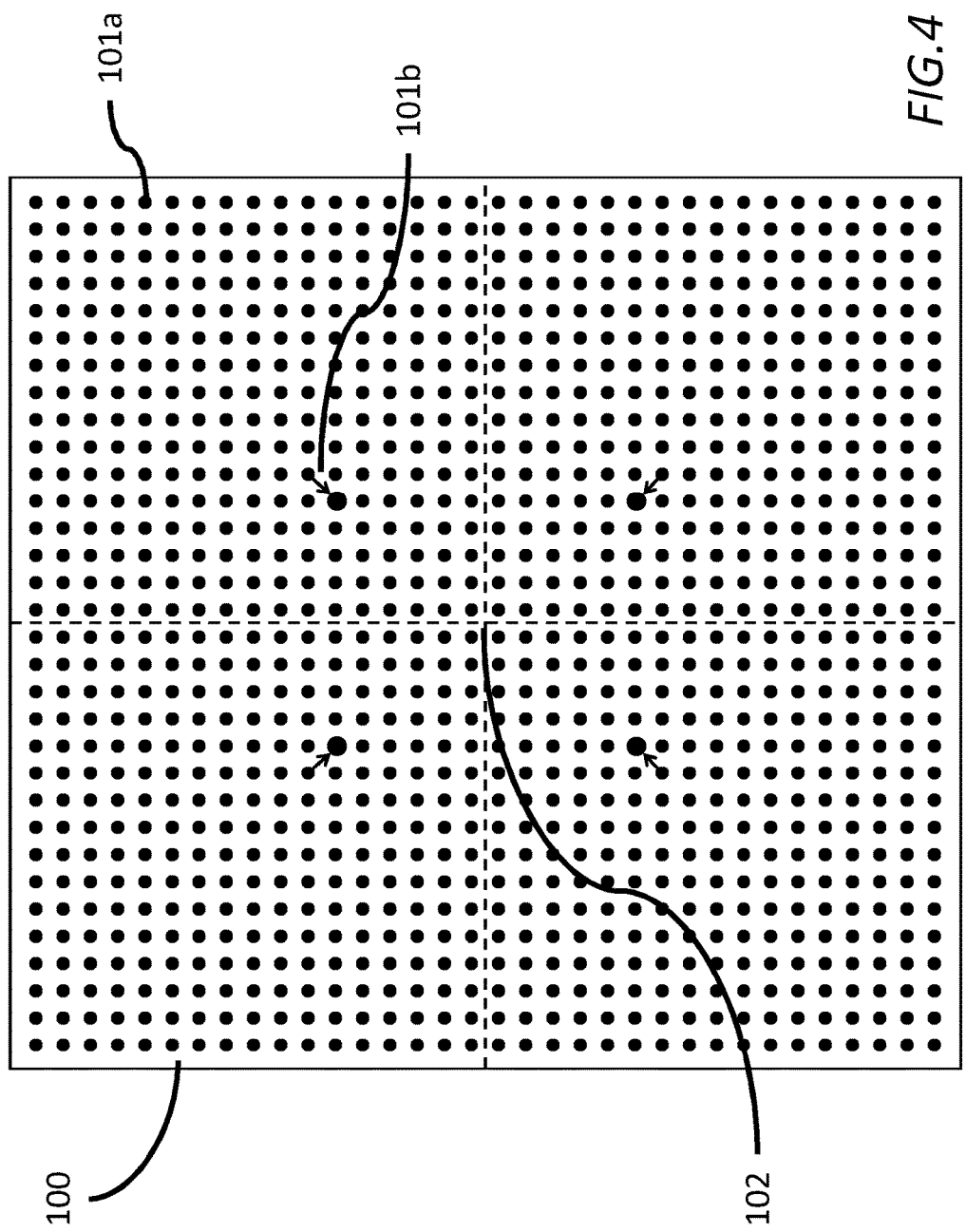
FIG. 4 is a plan view of a calibration sheet for use in the methods described herein.

Conventional methods of calibrating a computer vision system involve capturing a set of calibration images for each image capture device/camera that include multiple images of a calibration object of known size and with a known arrangement of calibration markings at various orientations and various locations within the field of view of the image capture device/camera. Such a calibration object typically takes the form of a calibration sheet, and FIG. 4 illustrates a plan view of an exemplary calibration sheet 100 comprising a 70×70 cm sheet of flat rigid material such as aluminium or steel on which a pattern revealing a 34×32 matrix of markings/circles 101a at known positions on the surface of the sheet is provided. Additionally in this example, towards the centre of the calibration sheet are four smaller markers 101b adjacent to four circles the centres of which together identify the four corners of a square of known size, and also a cross 102 formed by a pair of dashed lines which meet at the centre of the sheet 100.

By way of further example, MVTec Software GmbH provide calibration sheets in a range of sizes that are intended for use with their HALCON machine vision software package, and these calibration sheets comprise a 7×7 matrix of markings/circles.

Figure 5A:
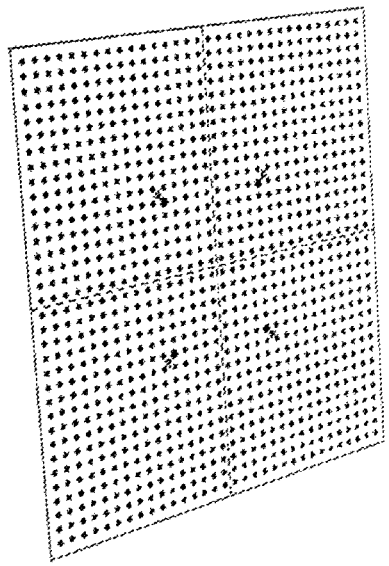
FIGS. 5A-D are illustrative examples of images of the calibration sheet of FIG. 4 illustrating the results of a number of different image distortions.
Figure 5B:
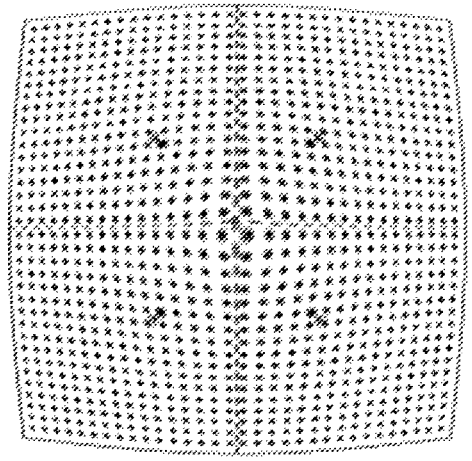
Figure 5C:
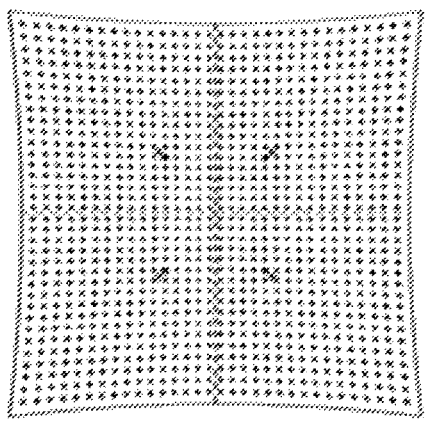
Figure 5D:
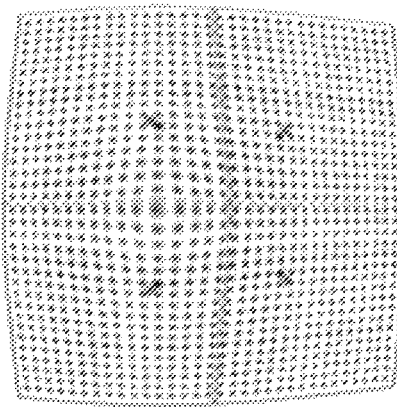

FIGS. 5A-D illustrate a set of images of the calibration sheet of FIG. 4. FIG. 5A illustrates an example of an image of the calibration sheet 100 as viewed from an angle. FIG. 5B illustrates an example of an image of the calibration sheet 100 in which barrel radial distortion is present, FIG. 5C illustrates an example of an image of the calibration sheet 100 in which pincushion radial distortion is present, and FIG. 5D illustrates an example of an image of the calibration sheet 100 in which de-centring distortion is present.

If images of a calibration sheet 100 of known size and with a known set of markings are obtained by each image capture device/camera, parameters defining the relative locations and orientations of the image capture devices/cameras of the system can be derived, as can parameters defining the internal characteristics of each of the image capture devices/cameras (e.g. the focal length, radial distortion coefficients, tangential distortion coefficients etc.). Thus for example in the case of FIG. 5A if the size and position of various markings of the calibration sheet 100 are known, the relative orientation of the sheet and a camera obtaining an image such as is shown in FIG. 5A can be determined. If an affine transformation is applied to such an image to remove distortions arising due to viewing the calibration sheet 100 from an oblique angle, then the view of the calibration sheet 100 should correspond to the plan view shown in FIG. 4. To the extent that any of the array of markers does not correspond to the plan view of FIG. 4 due to distortions arising from the internal characteristics of the image capture device/camera, such as are illustrated in FIGS. 5B-D, then these can be identified so that appropriate corrections for these distortions can be made before processing images to generate 3D models based on captured images.

Figure 6A:
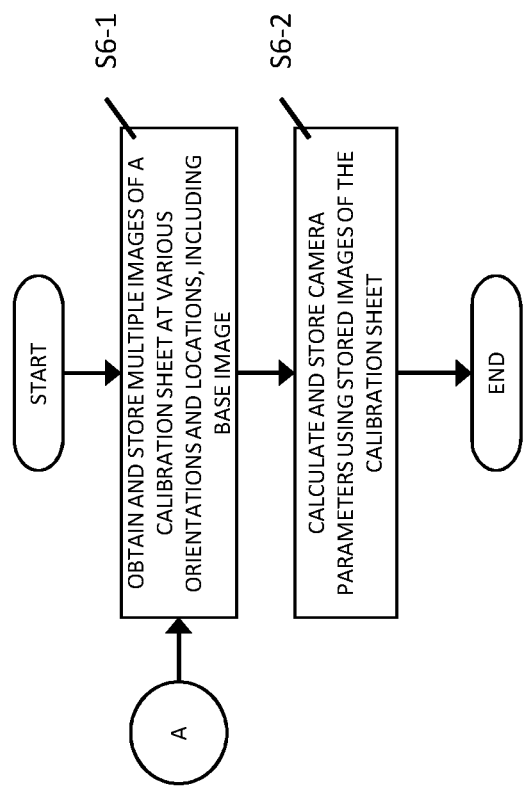

FIGS. 6A and 6B are a flow diagram illustrating the improved process of calibrating and operating a patient monitoring system/stereoscopic camera system in accordance with the present invention.

Initially, the patient monitoring system/stereoscopic camera system undergoes a full calibration, as illustrated in FIG. 6A, to establish camera parameters for each of the image capture devices/cameras of the system.

In FIG. 6A, in the first step of this full calibration of an image capture device/camera (s6-1), the image capture device/camera is used to obtain and store a set of calibration images for the image capture device/camera that includes multiple images of a calibration sheet with a known arrangement of calibration markings at various orientations and various locations within the field of view of the image capture device/camera.

This set of calibration images comprises a number of images (e.g. 10 to 15 different images) of the calibration sheet at different positions and orientations within the field of view of the image capture device/camera being calibrated. One of these images is designated as a base image for the calibration process and the surface of the calibration sheet in the base image is used to define a plane z=0 of a global co-ordinate system defined for the system.

The set of calibration images of the calibration sheet, including the base image, are then processed using information regarding the expected locations of the markings on the calibration sheet to determine camera parameters for the image capture device/camera that captured the set of calibration images and these camera parameters are then stored (S6-2).

The full calibration procedure illustrated in FIG. 6A is undertaken for each of the image capture devices/cameras until camera parameters have been calculated and stored for all of the image capture devices/cameras of the system. This determination of camera parameters for each image capture device/camera is done using conventional techniques.

By way of example, each of the calibration images within a set can be processed to extract the coordinates within the image of the markings on the calibration sheet. These coordinates can then be compared with the expected locations of the markings in the coordinate system to determine the parameters identifying the relative position and orientation of cameras and parameters internal to the cameras themselves (e.g. lens distortion, focal length, aspect ratio etc.), as is described in detail in "A Versatile Camera Calibration Technique for High-Accuracy 3D Machine Vision Metrology Using Off the Shelf TV Cameras and Lenses", Roger Tsai, IEEE Journal of Robotics and Automation, Vol. Ra-3, No. 4, August 1987 which is hereby incorporated by reference. As a further example, the HALCON machine vision software package from MVTec Software GmbH implements an alternative technique for determining a set of camera parameters for a camera from a set of calibration images, as is described in "Solution Guide III-C—3D Vision" issued by MVTec Software GmbH.

The stored camera parameters can then be used by the patient monitoring system when monitoring a patient to process the images captured by the image capture device/camera (e.g. to remove distortions from images and to convert matches between portions of different images into 3D surface measurements based upon the locations of relative matches in images and the relative locations and orientations of the cameras used to capture the images).

At some time after the full calibration has been completed, a re-calibration is initiated. Such an initiation of the re-calibration could be a manual action in which the re-calibration is initiated by the system operator at the start of the day or even between patients.

FIG. 6B is a flow diagram illustrating this re-calibration procedure, during which each image capture device/camera of the system undergoes a degree of re-calibration In a first step of the re-calibration procedure, the image capture device/camera undergoing re-calibration is used to obtain an additional image of a calibration sheet (S6-3), with the calibration sheet preferably placed at or close to a location to define the plane z=0 of a global co-ordinate system defined for the system. The placement of the calibration sheet 100 at the desired location can be achieved by placing the calibration sheet 100 on the surface of the mechanical couch 18 and locating the sheet with the centre of the sheet 100 located at the iso-centre of the treatment apparatus 16. In many cases the accurate placement of the sheet can be facilitated using laser light to highlight the location of the iso-centre as is often used in conventional radiotherapy apparatus and positioning and aligning the sheet 100 and the cross 102 on the sheet 100 with the projected planes of laser light. This additional image is then used to implement a calibration check to confirm whether or not the stored internal camera parameters for the image capture device/camera (i.e. the camera parameters relating to the internal characteristics of the camera) are still valid/accurate (S6-4) which may not be the case if for example the cameras have been knocked or otherwise have move out of position.

There are a number of possible methods by which an additional image can be used to confirm whether or not the stored internal camera parameters for an image capture device/camera are still valid/accurate.

By way of example, in order to check the accuracy of the previously stored camera parameters, the additional image can be processed using the previously stored camera parameters identifying the location and orientation of the image detectors and the internal camera characteristics to determine the location and orientation of the calibration sheet relative to the image detector. A back-projection of the markings on the calibration sheet onto the image plane can then be implemented using the determined location and orientation of the calibration sheet and the stored camera parameters. The accuracy of the stored internal camera parameters for a particular image capture device/camera can then be determined by comparing the appearance of the markings on the calibration sheet within the additional image captured by the image capture device/camera with the appearance of the calibration object in the back-projection. This comparison will then reveal any changes in the internal characteristics of the image detector. The back-projection would make use of data describing the calibration object and the locations of the marking on the calibration object.

As an alternative, the accuracy of the previously stored camera parameters relating to internal aspects of the cameras (e.g. lens distortion, focal length, aspect ratio etc.), could be determined by re-calculating these camera parameters using both the additional image and the previously stored images from the set of calibration images used in the initial calibration calculation. The re-calculated camera parameters relating to internal aspects of the image capture device/camera can then be compared with the corresponding stored camera parameters relating to these internal aspects that were calculated for the image capture device/camera during the initial full calibration process to determine if there is a substantial difference between the re-calculated parameters and the stored parameters, and therefore whether or not the stored camera parameters relating to the internal aspects of the cameras are still accurate.

For example, this could involve calculating the difference between the values of each of the re-calculated camera parameters relating to internal aspects of the camera and the values of the corresponding stored internal camera parameters, and determining if any of these differences exceed a corresponding threshold.

If it is determined that the stored camera parameters relating to internal characteristics of the camera resulting from the last full calibration are still sufficiently accurate (i.e. that the detected change in the camera parameters or that the differences between imaged and projected positions for markings on a calibration sheet differ by less than a threshold amount), then the image capture device/camera can be partially re-calibrated, without having to undertake a full calibration process that would require an entirely new set of calibration images. This can be achieved by replacing the previously stored base image with the newly captured image (S6-8), and then re-calculating the camera parameters using the stored calibration images, which now include the newly captured image (S6-9).

This re-calibration can be achieved without having to obtain a completely new set of calibration images as if it is determined that the camera parameters relating to internal aspects of the cameras are still sufficiently accurate (i.e. that none of the cameras internal characteristics have appear to have changed significantly) the stored images can be reused together with the new base image to calibrate the system. This is even the case if the cameras have been knocked out of position in the period of time between obtaining the original set of camera images (s6-1) and the new additional image (s6-3). This is because any movement of the image capture device/camera can be taken into account by using the new image as the basis for determining the current location and orientation of the cameras.

If it is determined that the internal characteristics of the image detector appear to have changed significantly, then a full recalibration will be required. For example, this could be because some internal aspect of the camera has been adjusted intentionally or unintentionally. When this occurs, the system therefore determines that a full recalibration of this image capture device/camera is required (S6-10) and indicates this to the operator. The process therefore proceeds to implement a full recalibration (i.e. returns to step S6-1) requiring full recalibration using an entirely new set of calibration images.

When a re-calibration has been initiated, the procedure illustrated in FIG. 6B is repeated until camera parameters have been re-calculated and stored for all of the image capture devices/cameras of the system. The system then awaits the initiation of the next re-calibration check.

In the above described embodiment of the calibration process, the initial full calibration, the calibration check, and the full and partial recalibration of the patient monitoring system are described as making use of images of a calibration object in the form of a calibration sheet 100. Whilst each of these steps could be implemented using the same calibration object, or at least a calibration object of the same design, it is also equally possible to make use of a different form/design of calibration object for each step, provided that the form/design of the calibration object is sufficient to allow the 3D location and orientation of the calibration object to be determined and provided that the system has data describing each calibration object. For example, a first calibration object could be used when obtaining the set of calibration images for the initial full calibration, a second calibration object could then be used when obtaining the additional image for the calibration check (with the additional image of this second calibration object also being used for a partial recalibration), and a third calibration object could then be used when obtaining the further set of calibration images for a full recalibration.

In a particularly advantageous embodiment, a first calibration object is used to implement the initial full calibration, whilst a second calibration object is used to implement the calibration check and any partial recalibration. The first calibration object should then be reused should a full recalibration be required. This approach can then make use of a first calibration object that is more expensive than the second calibration object, with the first calibration object being made temporarily available by the manufacturer/supplier of the patient monitoring system as and when required for infrequent full calibrations, and the second calibration object being supplied to the end user of the patient monitoring system for the more regular partial recalibrations.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means. When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

The invention claimed is:

1. A method of calibrating a patient monitoring system the method including:
using an image detector of the patient monitoring system in a fixed location to obtain a set of calibration images comprising images of a calibration object at various orientations and locations;
storing the obtained calibration images;
processing the stored calibration images to calculate parameters defining the location and orientation of the viewpoint of the image detector and parameters identifying internal characteristics of the image detector, and storing the calculated parameters; and
subsequently re-calibrating the patient monitoring system by:
obtaining an additional image of a calibration object using the image detector;
using the stored calibration images and the additional image to calculate a parameter identifying an internal characteristic of the image detector;
if the calculated parameter identifying an internal characteristics of the image detector differs by more than a threshold amount from an expected value, obtaining a further set of calibration images using the image detector and recalculating the camera parameters for the image detector using the further set of calibration images; and
if the calculated parameter identifying an internal characteristic of the image detector does not differ by more than a threshold amount from an expected value, recalculating the camera parameters for the image detector using the stored set of calibration images and the additional image of the calibration object obtained by the image detector.

2. The method of claim 1, wherein the expected value of a calculated parameter identifying an internal characteristic of the image detector is the value of the calculated parameter identifying the internal characteristic of the image detector calculated on the basis of the previously stored calibration images.

3. A method of calibrating a patient monitoring system the method comprising:
using an image detector of the patient monitoring system to obtain a set of calibration images comprising images of a calibration object at various orientations and locations;
storing the obtained calibration images;
processing the stored calibration images to calculate camera parameters defining the location and orientation of the image detector and parameters identifying internal characteristics of the image detector, and storing the calculated parameters; and
subsequently re-calibrating the patient monitoring system by:
obtaining an additional image of a calibration object using the image detector;
processing the additional image utilizing the stored camera parameters to determine the location and orientation of the calibration object relative to the image detector;
determining a back-projection of the expected appearance of the calibration object onto the image plane of the image detector utilizing the stored camera parameters and the determined location and orientation of the calibration sheet;
if the appearance of the calibration object within the additional image captured by the image capture detector and the back-projection of the calibration object differ by more than a threshold amount, obtaining a further set of calibration images using the image detector and recalculating the camera parameters for the image detector using the further set of calibration images; and if the appearance of the calibration object within the additional image captured by the image capture detector and the back-projection of the calibration object does not differ by more than a threshold amount, recalculating the camera parameters for the image detector using the stored set of calibration images and the additional image of the calibration object obtained by the image detector.

4. The method of claim 1, wherein, recalculating a camera parameter for an image detector using the stored set of calibration images and the additional image of the calibration object obtained by the image detector comprises calculating the location and orientation of the viewpoint of the image detector and internal characteristics of the image detector utilizing the additional image as a base image relative to which the other images are compared.

5. The method of claim 1, wherein the calibration object used when obtaining the set of calibration images differs from the calibration object used to obtain the additional image.

6. The method of claim 5, wherein the calibration object used when obtaining a further set of calibration images is the same as the calibration object used when obtaining the set of calibration images.

7. The method of claim 1, wherein the calibration object comprises a calibration sheet.

8. The method of claim 7, wherein the additional image comprises an image of a calibration sheet located directly on a measurement plane of the patient monitoring system.

9. The method of claim 8, wherein the measurement plane of the patient monitoring system is defined as $z=0$ plane of a global co-ordinate system defined for the patient monitoring system.

10. The method of claim 9, wherein the global co-ordinate system defined for the patient monitoring system is that used to generate 3D wire mesh models of the surface of a patient monitored by the system.

11. The method of claim 1, wherein a set of calibration images comprises at least 10 images of a calibration object at various orientations and various locations within a field of view of an image detector.

12. The method of claim 1, wherein the patient monitoring system comprises a stereoscopic camera system comprising a plurality of image detectors and calibrating the patient monitoring system comprises calibrating each of the image detectors.

13. The method of claim 1, wherein the re-calibration of the patient monitoring system is repeated periodically.

14. The method of claim 13, further comprising using the patient monitoring system to monitor the position of a patient between obtaining images of the calibration object and the re-calibration of the patient monitoring system.

* * * * *